US006303740B1

(12) United States Patent
Singh

(10) Patent No.: US 6,303,740 B1
(45) Date of Patent: Oct. 16, 2001

(54) POLYMOLECULAR STRUCTURES FORMED BY COMPLEMENTARY ASSOCIATION OF AMPHIPHILIC TARTARIC ACID DERIVATIVES AND BIPYRIDINE COMPOUNDS

(75) Inventor: Alok Singh, Springfield, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/386,440

(22) Filed: Aug. 31, 1999

(51) Int. Cl.$^7$ .................................................. C08G 69/44
(52) U.S. Cl. ...................... 528/289; 528/271; 528/298; 528/494; 528/503; 524/261; 524/366
(58) Field of Search ..................... 528/271, 289, 528/298, 494, 503; 524/261, 366

(56) References Cited

U.S. PATENT DOCUMENTS

| 5,037,574 | 8/1991 | Frechet et al. ................... 252/299.01 |
| 5,139,696 | 8/1992 | Frechet et al. ................... 252/299.01 |

OTHER PUBLICATIONS

Kihara et al, "Supramolecular Liquid–Crystalline Networks Built by Self–Assembly of Multifunctional Hydrogen–Bonding Molecules", Chem. Mater., vol. 8, No. 4 (1996), pp. 961–968.

Kato et al, "Cooperation of Hydrogen Bonds for Mesophase Stabilization in Supramolecular Assemblies", Chemistry Letters 1997, pp. 1143–1144.

Kihara et al, "Induction of a Cholesteric Phase via Self–Assembly in Supramolecular Networks Built of Non–Mesomorphic Molecular Components" Liquid Crystals, 1998, vol. 24, No. 3, pp. 413–418.

Mallia et al Photochemical Phase Transition in hydrogen–Bonded Liquid Crystals, Chem. Mater 1999, 11, pp 207–208.

J. –M. Lehn, "Supramolecular Chemistry: Concepts and Perspectives" published by Verlag Chemie, Weinheim, pp139–197, (1995).

C. P. Lillya et al., "Linear Chain Extension Through Associative Terminii", Macromolecules, 25, 2076–2080 (1993).

R. P. Sijbesma et al., "Reversible Polymers by Quadruple Hydrogen Bonding", Science, 278, 1601–1604, (1997).

T. Kato, "A Liquid Crystalline Polymer Network Built by Molecular Self–Assembly Through Intermolecular Hydrogen Bonding", Angew. Chem. Int. Ed. Engl., 33,1644, (1994).

*Primary Examiner*—Samuel A. Acquah
(74) *Attorney, Agent, or Firm*—John J. Karasek; Amy L. Ressing

(57) ABSTRACT

Self-organized polymolecular structures, including structures having a helical, tubular or needle-like morphology, are formed by the association of molecules of an amphiphilic 2,3 di-O-substituted tartaric acid compound and molecules of a bipyridyl compound. If the tartaric compound includes a polymerizable functional group, the polymolecular structures may be stabilized by polymerization.

16 Claims, No Drawings

US 6,303,740 B1

POLYMOLECULAR STRUCTURES FORMED BY COMPLEMENTARY ASSOCIATION OF AMPHIPHILIC TARTARIC ACID DERIVATIVES AND BIPYRIDINE COMPOUNDS

BACKGROUND OF THE INVENTION

1. Field of the Invention

The invention relates generally to self-organized polymolecular structures and in particular, to helical, tubular and needle-like structures formed by the association of amphiphilic tartaric acid derivatives and bipyridine compounds.

2. Description of the Related Art

Materials of defined morphologies, such as polymolecular tubular or helical structures, have many practical uses, including as vehicles for controlled-release drug delivery, as reinforcing material for high strength composites and as components of radar absorbing materials.

Currently known materials of defined morphologies include structures formed by molecular self-assembly of single molecular components such as amphiphiles (for example, phospholipids). Amphiphiles are compounds that have a hydrophobic portion and a hydrophilic portion. In an aqueous solution, the hydrophobic portions of adjacent molecules tend to congregate, thereby creating a polymolecular structure. For example, U.S. Pat. No. 5,290,960 to Singh describes tubular microstructures formed by the self-assembly of diacetylenic phospholipids. The technical utility of diacetylenic phospholipid-derived tubules for applications such as controlled release drug delivery has been demonstrated, but the practical usefulness of these materials is limited because of their high cost and poor shelf life.

Self organized structures have also been formed by the non-covalent interactions (such as hydrogen bonding) between complementary molecular building blocks. Such structures are described, for example, in the following publications, incorporated herein by reference: J. -M. Lehn, "Supramolecular Chemistry: Concepts and Perspectives" published by Verlag Chemie, Weinheim, pp 139–197, (1995); C. P. Lillya et al., "Linear Chain Extension Through Associative Terminii", Macromolecules, 25, 2076–2080, (1993); R. P. Sijbesma et al., "Reversible Polymers by Quadruple Hydrogen Bonding", Science, 278, 1601–1604, (1997); T. Kato, "A Liquid Crystalline Polymer Network Built by Molecular Self-Assembly Through Intermolecular Hydrogen Bonding", Angew. Chem. Int. Ed. Engl., 33, 1644, (1994); C. M. Paleos and D. Tsiourvas, Angew. Chem. Int. Ed. Engl., 34, 1696–1711, (1995) and G. Whitesides et al., Non-covalent Synthesis, Acc. Chem. Res., 28, 1, 1995. Intermolecular hydrogen bonding between compounds containing pyridine groups and compounds containing carboxyl groups is described in the following patents and publications, incorporated herein by reference: U.S. Pat. No. 5,037,574 to Frechet et al; U.S. Pat. No. 5,139,696 to Frechet et al; Kihara et al, "Supramolecular Liquid-Crystalline Networks Built by Self-Assembly of Multifunctional Hydrogen-Bonding Molecules", Chem. Mater., Vol 8, No. 4 (1996), pp 961–968; Kato et al, "Cooperation of Hydrogen Bonds for Mesophase Stabilization in Supramolecular Assemblies", Chemistry Letters 1997, pp 1143–1144; Kihara et al, "Induction of a Cholesteric Phase via Self-Assembly in Supramolecular Networks Built of Non-Mesomorphic Molecular Components" Liquid Crystals, 1998, Vol. 24, No. 3, pp. 413–418; and Mallia et al "Photochemical Phase Transition in hydrogen-Bonded Liquid Crystals," Chem. Mater 1999, 11, pp 207–208.

SUMMARY OF THE INVENTION

It is an object of this invention to provide a method to make polymolecular structures with inexpensive molecular building blocks.

It is a further object of this invention to exploit both the ability of amphiphiles to self-assemble by hydrophobic interactions to form microstructures and the ability of compounds having complementary hydrogen-bonding functional groups to self-organize to form supramolecular systems.

It is a further object of this invention to provide stable polymolecular structures having defined morphologies.

It is a further object of this invention to provide polymolecular structures wherein functional groups such as chromophoric functional groups, electrically-conducting functional groups, or a metal chelating groups are incorporated into the structure.

These and other object of the invention are accomplished by a composition comprising a self-organized polymolecular association of molecules of a 2,3 di-O-substituted tartaric acid compound and molecules of a bipyridyl compound. Helical, tubular or needle-like structures can be made by combining the tartaric acid compound and bipyridyl compound and heating the mixture so that the two components are mixed on a molecular level and interact to form self-organized polymolecular structures.

DETAILED DESCRIPTION OF THE PREFERRED EMBODIMENT

In the present invention, materials with unique defined structural and morphological properties are formed by the noncovalent association of complementary monomers, specifically, tartaric acid derivatives and bipyridine compounds.

The tartaric acid derivative of the present invention is a tartaric acid compound that has been modified to give it an amphiphilic character by replacing the middle hydroxyl groups with hydrophobic moieties such as alkoxy groups. The substituted hydrophobic groups may also incorporate functional moieties such as chromophoric functional groups, electrically-conducting functional groups, metal chelating groups or polymerizable groups.

Examples of chromophoric functional groups include, but are not limited to, substituted azobenzene, stilbene, and biphenyl groups.

Examples of electrically-conducting functional groups include, but are not limited to cyanobenzene, furan, pyrrole and thiophene groups Examples of metal-chelating groups, but are not limited to crown ethers, N-substituted crown ethers, and amine groups.

Examples of polymerizable groups include, but are not limited to methacryloyl, vinylbenzyl, dienyl, diacetylenic, and sulfhydryl groups.

In general, the tartaric acid derivative may be represented by the formula (1):

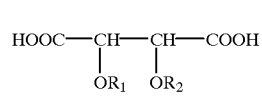

(1)

wherein $R_1$, and $R_2$ are the same or different and are selected from the group consisting of —H, wherein $R_1$ and $R_2$ are not both H —$(CH_2)_a$—$CH_3$, wherein a is an integer between 0 and 20, —$(CH_2)_b$—X, wherein b is an integer between 0 and 20 and X is a polymerizable group, —$(CH_2)_c$—X—$(CH_2)_d$—$CH_3$, wherein c and d are integers between 0 and 20, wherein the sum of c and d is not greater than 20 and wherein X is as defined above, —(CH$_2$)$_e$—X—(CH$_2$)$_f$—Y, wherein e and f are integers between 0 and 20, wherein the sum of e and f is not greater than 20, wherein X is as defined above, and wherein Y is a functional group selected from the functional groups consisting of a chromophoric functional group, and electrically-conducting functional group, and a metal chelating group, —(CH$_2$)$_g$—Y—(CH$_2$)$_h$—X, wherein g and h are integers between 0 and 20, wherein the sum of g and h is not greater than 20, and wherein X and Y are as defined above, —(CH2)$_i$—X—(CH$_2$)$_j$—Y—(CH$_2$)$_k$—CH$_3$, wherein i, j, and k are integers between 0 and 20, wherein the sum of i, j, and k is not greater than 20, and wherein X and Y are as defined above, and —(CH$_2$)$_l$—Y—(CH$_2$)$_m$—X—(CH$_2$)$_n$—CH$_3$, wherein l, m, and n are integers between 0 and 20, wherein the sum of l, m, and n is not greater than 20, and wherein X and Y are as defined above.

The tartaric acid derivative used in the present invention may be derived from the L-tartaric acid, D-tartaric acid, or DL tartaric acid. Preferably, the L-form is used because, as a byproduct of the wine industry, it is relatively inexpensive. The derivative may be formed by any method known in the art such as, for example, reacting N,N,N'N'-tetramethyl-tartaramide (commercially available starting material) with a substituted bromide in the presence of thallium ethoxide or sodium hydride in dimethylformamide (DMF) (preferred) and then hydrolyzing the substituted amide. This synthesis is represented by the following reaction scheme:

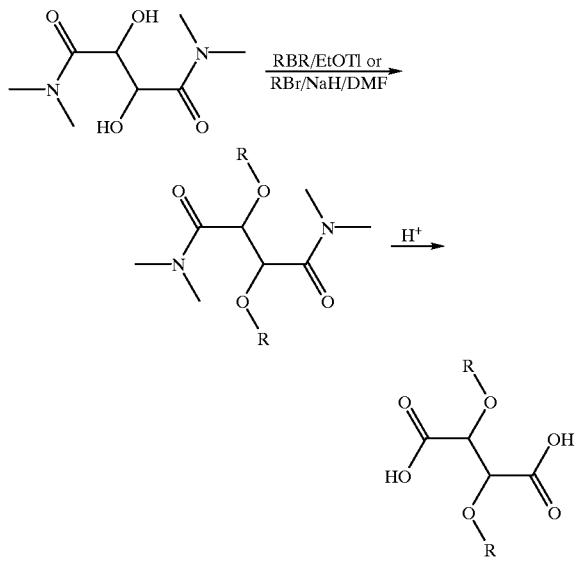

Because additional and expensive synthesis steps would be required to produce a tartaric acid derivative having different substituents for R$_1$ and R$_2$, it is preferable that R$_1$ and R$_2$ be the same.

In the present invention, the tartaric acid derivative associates by intermolecular hydrogen bonding with a bipyridine compound to form a self-organized polymolecular structure. Preferably, the bipyridine compound is 2,2-bipyridine or 4,4-bipyridine. The polymolecular association of a tartaric acid derivative with 4,4-bipyridine may be depicted as follows:

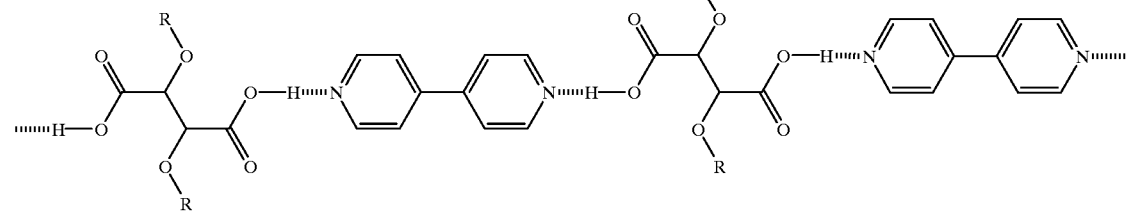

The polymolecular association of a tartaric acid derivative with 2,2-bipyridine may be depicted as follows:

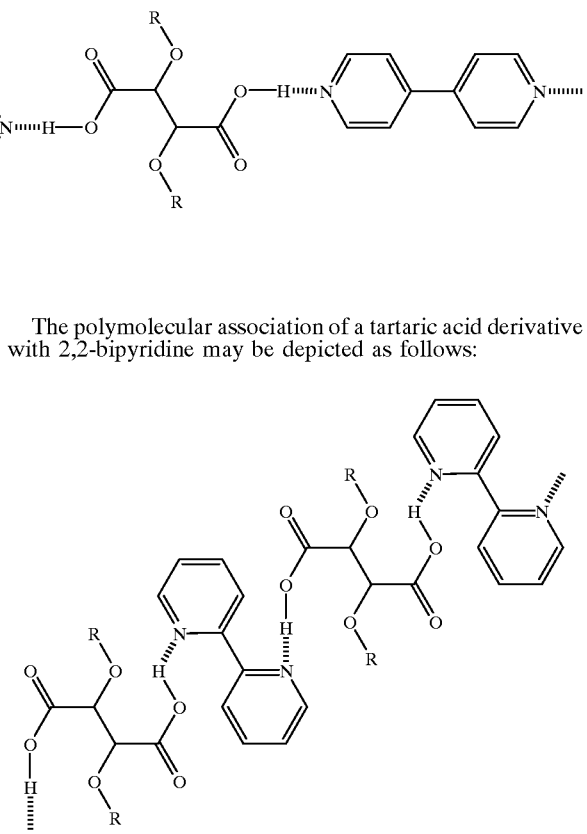

Examples of other bipyridine compounds that could be used include compounds represented by the formulas

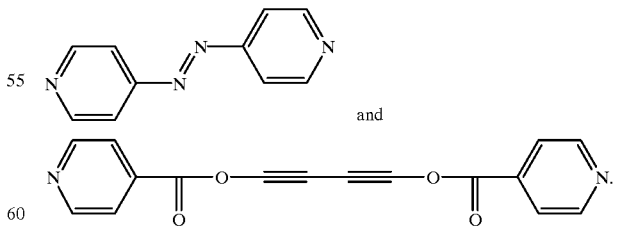

The tartaric acid derivative and the bipyridine compound may be mixed by any method known in the art, such as, for example, by preparing a solution of each component in methylene chloride under an inert atmosphere and then combining the two solutions. Preferably, the tartaric acid derivative and the bipyridine compound are combined in equimolar amounts. To create a polymolecular association, the solvent is removed in a stream of nitrogen and the resulting solid mass is heated, typically to about 160–170° C. for about 30–40 seconds. Cooling the heated solid mass creates a glassy or polycrystalline material that can be stored in an inert atmosphere.

To create helical or tubular structures that can exist at room temperature, the glassy or polycrystalline mixture of the tartaric acid derivative and the bipyridine compound may be combined with an aprotic solvent such as silicone oil or a protic solvent such as ethanol, then heated to a temperature just below the phase transition temperature and then allowed to cool to room temperature. The solvent should be selected as one that has a relatively high boiling point and that is not reactive with either the tartaric acid derivative or the bipyridine compound. Ethanol is a suitable protic solvent because it is inexpensive, environmentally safe, and less competitive than the acid functionality of tartaric acid in forming a hydrogen bond.

By choosing an appropriate solvent and an appropriate polymerizable functional group, it is possible to achieve a monodispersed population of structures. For example, in the case of ethanol derived structures, multiple populations having different melting points are produced (as discussed below). Lower melting point structures can be eliminated if stabilization (polymerization) is carried out at a temperature above the melting point of these structures. For example, if the sample is stabilized by polymerization at 85° C., then structures that melt below this temperature will be melted and can be removed, and only the structures that melt above this temperature will be stabilized.

If the tartaric acid derivative contains polymerizable groups, the helical or tubular structures may be further stabilized by causing the polymerizable groups on adjacent molecules of the tartaric acid derivative to polymerize.

Polymolecular structures of the present invention may be used as templates for the formation of metallic or ceramic microstructures. For example, polymolecular structures having a needle-like morphology may be surrounded by metal or by ceramic precursors in an aprotic solvent to form metal or ceramic tubular or cylindrical structures. Polymolecular structures having chromophoric functional groups may be used in forming films, surfaces and structures having useful optical properties. In particular, chromophoric structures that have a needle-like morphology and that are unidirectionally aligned on a substrate will have nonlinear optical properties. Polymolecular structures having electrically conducting functional groups may be used in the formation of molecular wires and for making conductive films and surfaces. Polymolecular structures having metal chelating groups may be used as filters for sequestering heavy metal ions. Structures that are stabilized by polymerization may be used as a component in nanocomposite materials or to encapsulate substances for controlled release. Other uses for the polymolecular structures of the present invention will be readily apparent to persons skilled in the art.

Having described the invention, the following examples are given to illustrate specific applications of the invention, including the best mode now known to perform the invention. These specific examples are not intended to limit the scope of the invention described in this application.

EXAMPLES

Both 2,2'- and 4,4'-bipyridines Were Purchased from Commercial Sources and Recrystallized from Toluene Before Use Preparation of 1,2-Dioctdecyloxy-L-tartaric Acid:

1,2-Dioctadecyloxy-L-tartaric acid (TA-O18) was synthesized following the synthetic route depicted above, using octadecyl bromide as the substituted bromide; the reaction of N, N, N'N'-tetramethyl-tartaramide with octadecyl bromide in the presence of thallium ethoxide or sodium hydride in dimethylformamide provided N,N,N',N'-tetramethyl, 1,2-dioctadecyloxy-L-tartaramide. The tartaramide was converted into the tartaric acid derivative by hydrolyzing it with 20% HCl at 80 C. 1,2-Dioctadecyloxy-L-tartaric acid was crystallized with hot hexane and dried under vacuum before starting each experiment.

Preparation of 1,2-Dibutoxy-L-tartaric Acid:

Following the protocol described above, N,N,N'N'-tetramethyl-tartaramide was reacted with butyl bromide in the presence of sodium hydride in dimethylformamide. After acid-catalyzed hydrolysis, 1,2-dibutoxy-L-tartaric acid was isolated in yields higher than 80%.

Preparation of Self-organized Polymolecular Associations:

Samples of mixtures of 1,2-dioctadecyloxy-L-tartaric acid and either 2,2-bipyridine or 4,4-bipyridine were prepared and stored under nitrogen atmosphere. Typically, a methylene chloride solution of each component was mixed to attain desired molar ratio of components. The solvent was then removed in a stream of nitrogen and the resulting solid mass was heated at 170° C. for 40 seconds, and dried under vacuum for several hours. Usually a polycrystalline material turns sticky solid due to linear polymolecular association;. IR (Nicolet FT-IR) and NMR (BRUKER DRX-400, 400 MHz FT-NMR) were used to characterize the starting materials and their mixtures. The IR spectrum was recorded on thin film of material directly spread from its methylene chloride solution to a KBr pallet with the aid of a slow nitrogen stream. Alternatively, KBr pallets were also made to record spectra. No difference in spectra was noticed between either of two techniques. Absorption at 1916, 2460 and 1726 $cm^{-1}$ in IR spectrum confirmed the formation hydrogen bonded association.

Characterization of Microscopic Structures:

Differential scanning calorimetric (DSC) studies were performed with a Perkin-Elmer DSC-7 instrument. Polycrystalline materials made by association of complementary molecules were sealed in stainless pans and the samples were scanned for both cooling and heating transitions. In the cases where dispersion medium is involved, the samples were thermally equilibrated before recording any scans. Solid materials showed melting transition at 157° C., which is larger than either of the precursor materials. Several small peaks were observed before main chain melting, showing that the material may be polydispersed in nature and that several phases exist before material melted.

Microscopic Structure Formation and Visualization:

Organized structure optical microscopic studies were conducted on a Nikon model diathote inverted optical microscope equipped with a temperature controlled stage and a camera to record the images.

Structures in Solid State:

Needle-like structures were formed by heating the polycrystalline sticky complex made by association of 1,2-dioctadecyloxy-L-tartaric acid and 4,4 bipyridine. The needles were seen formed by rolling of ribbons in a helical manner and existed between 100 and 145° C. This large temperature range may be due to polydispersity in the linear polymer. The large temperature range is advantageous because is provides a large working temperature window. These structures are obtained only through the association of the two starting materials and cannot be obtained by heating either component in the absence of the other.

A different morphology of higher ordered material was observed by the association of 1,2-dioctadecyloxy-L-tartaric acid and 2,2 bipyridine.

By lowering the temperature of the mixtures to 100° C. and below, all these morphologies were lost, and a textureless morphology was observed. However, the process of making structures materials was found to be reversible.

Upon heating the mixtures back to 140° C. and holding the material at that temperature or upon heating the mixtures until the material melts and then cooling, needlelike textures could be produced in the same temperature range as observed earlier.

Structures in Silicone Oil (An Aprotic Solvent):

The polycrystalline material was combined with silicone oil to form a dispersion having a concentration of 47 mg/ml. This dispersion, when heated to 180° and cooled to room temperature, provided needle like structures. The DSC thermogram showed two major exothermic events peaked 126° C. and 36° C., indicating a continuous growth of needles, while upon heating, several endothermic peaks (>5) were observed, indicating melting of needles of various molecular weight ranges. In silicone oil, the material did not show any decomposition upon repeat heating, and high molecular weight structures were formed. On the average, 150 µm long needles were observed.

Structures in Ethanol (A Protic Solvent):

Example I

The polycrystalline material was combined with ethanol to form a dispersion having a concentration of 40 mg/mL solution. The mixture was heated until the polycrystalline material dissolved and then was allowed to cool to room temperature. Formation of a fine precipitate was observed which under a microscope revealed the formation of ribbon, helices and needle-like structures, some of which gave the appearance of tubules. More than 100 µm long structures were observed. Details of the needle images as observed under a confocal microscope indicated the existence of a hollow core in the needle structure, raising the likelihood that needles were tubules. The DSC thermogram revealed the formation of multiple populations of tubules, as confirmed by three sharp but large chain melting transition temperatures at 93, 75 and 51° C.

Example II

The polycrystalline material was dissolved in warm ethanol to form a clear solution (concentration of 10–40 mg/mL). To the warm ethanol solution, anhydrous hexane was added slowly until a white, cloudy solution was formed. The cloudy suspension was heated to make clear solution and was left to slowly cool to room temperature. Microscopic structures are formed which were separated by gentle centrifugation and re-suspended in hexane.

Obviously, many modifications and variations of the present invention are possible in light of the above teachings. It is therefore to be understood that, within the scope of the appended claims, the invention may be practiced otherwise than as specifically described.

What is claimed is:

1. A composition comprising a self-organized polymolecular association of molecules of an amphiphilic 2,3 di-O-substituted tartaric acid compound and molecules of a bipyridyl compound.

2. The composition of claim 1 wherein the polymolecular association has a helical, tubular or needle-like morphology.

3. The composition of claim 1 wherein the 2,3 di-O-substituted tartaric acid compound is a 2,3-dialkoxy tartaric acid.

4. The composition of claim 1 wherein the 2,3 di-O-substituted tartaric acid compound is 2,3-dioctadecyloxy-L-tartaric acid.

5. The composition of claim 1 wherein the bipyridyl compound is selected from the group consisting of 4,4' bipyridine and 2,2' bipyridine.

6. A composition comprising a polymolecular association of (a) a tartaric acid derivative represented by formula (1):

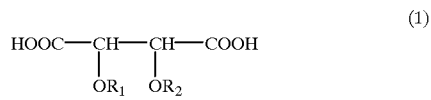

wherein $R_1$ and $R_2$ are the same or different and are selected from the group consisting of —H, provided that $R_1$ and $R_2$ are not both H, —$(CH_2)_a$—$CH_3$, wherein a is an integer between 0 and 20, —$(CH_2)_b$—X, wherein b is an integer between 0 and 20 and X is a polymerizable group, —$(CH_2)_c$—X—$(CH_2)_d$—$CH_3$, wherein c and d are integers between 0 and 20, wherein the sum of c and d is not greater than 20 and wherein X is as defined above, —$(CH_2)_e$—X—$(CH_2)_f$—Y, wherein e and f are integers between 0 and 20, wherein the sum of e and f is not greater than 20, wherein X is as defined above, and wherein Y is a functional group selected from the functional groups consisting of a chromophoric functional group, and electrically-conducting functional group, and a metal chelating functional group, —$(CH_2)_g$—Y—$(CH_2)_h$—X, wherein g and h are integers between 0 and 20, wherein the sum of g and h is not greater than 20, and wherein X and Y are as defined above, —$(CH2)_i$—X—$(CH_2)_j$—Y—$(CH_2)_k$—$CH_3$, wherein i, j, and k are integers between 0 and 20, wherein the sum of i, j and k is not greater than 20, and wherein X and Y are as defined above, and —$(CH_2)_l$—Y—$(CH_2)_m$—X—$(CH_2)_n$—$CH_3$, wherein l, m, and n are integers between 0 and 20, wherein the sum of l, m, and n is not greater than 20, and wherein X and Y are as defined above, and (b) a bipyridyl compound.

7. The composition of claim 6 wherein the bipyridyl compound is selected from the group consisting of 4,4' bipyridine and 2,2' bipyridine.

8. A method of making at least one helical or tubular polymolecular structure, the method comprising the steps of combining an amphiphilic 2,3 di-O-substituted tartaric acid compound and a bipyridyl compound in a first solvent to create a first mixture, removing the first solvent to create a solid mass, heating the solid mass to a first temperature sufficient to provide hydrogen bonding between molecules of the 2,3 di-O-substituted tartaric acid compound and molecules of the bipyridyl compound, and cooling the solid mass, combining the solid mass with a second solvent to create a second mixture heating the second mixture to a second temperature sufficient to dissolve the solid mass, and cooling the second mixture to form at least one helical or tubular polymolecular structure.

9. The method of claim 8 wherein the tartaric acid compound is represented by the formula (1):

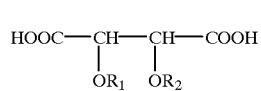

(1)

wherein $R_1$ and $R_2$ are the same or different and are selected from the group consisting of —H, provided that $R_1$ and $R_2$ are not both H, —$(CH_2)_a$—$CH_3$, wherein a is an integer between 0 and 20, —$(CH_2)_b$—X, wherein b is an integer between 0 and 20 and X is a polymerizable group, —$(CH_2)_c$—X—$(CH_2)_d$—$CH_3$, wherein c and d are integers between 0 and 20, wherein the sum of c and d is not greater than 20 and wherein X is as defined above, —$(CH_2)_e$—X—$(CH_2)_f$—Y, wherein e and f are integers between 0 and 20, wherein the sum of e and f is not greater than 20, wherein X is as defined above, and wherein Y is a functional group selected from the functional groups consisting of a chromophoric functional group, and electrically-conducting functional group, and a metal chelating functional group, —$(CH_2)_g$—Y—$(CH_2)_h$—X, wherein g and h are integers between 0 and 20, wherein the sum of g and h is not greater than 20, and wherein X and Y are as defined above, —$(CH2)_i$—X—$(CH_2)_j$—Y—$(CH_2)_k$—$CH_3$, wherein i, j, and k are integers between 0 and 20, wherein the sum of i, j, and k is not greater than 20, and wherein X and Y are as defined above, and —$(CH_2)_l$—Y—$(CH_2)_m$—X—$(CH_2)_n$—CH3, wherein l, m, and n are integers between 0 and 20, wherein the sum of l, m, and n is not greater than 20, and wherein X and Y are as defined above, and the bipyridyl is compound selected from the group consisting of 4,4' bipyridine and 2,2' bipyridine.

10. The method of claim 8 wherein the first solvent is methylene chloride.

11. The method of claim 8 wherein the second solvent is an aprotic solvent.

12. The method of claim 11 wherein the aprotic solvent is silicone oil.

13. The method of claim 8 wherein the solvent is a protic solvent.

14. The method of claim 13 wherein the solvent is ethanol.

15. A method of making at least one helical, tubular or needle-like structure, the method comprising the steps of combining (i) a 2,3 di-O-substituted tartaric acid derivative represented by formula (1):

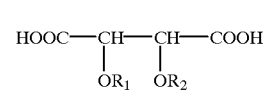

(1)

wherein $R_1$ and $R_2$ are the same or different and are selected from the group consisting of —$(CH_2)_b$—X, wherein b is an integer between 0 and 20 and X is a polymerizable group, —$(CH_2)_c$—X—$(CH_2)_d$—$CH_3$, wherein c and d are integers between 0 and 20, wherein the sum of c and d is not greater than 20 and wherein X is as defined above, —$(CH_2)_e$—X—$(CH_2)_f$—Y, wherein e and f are integers between 0 and 20, wherein the sum of e and f is not greater than 20, wherein X is as defined above, and wherein Y is a functional group selected from the functional groups consisting of a chromophoric functional group, and electrically-conducting functional group, and a metal chelating group, —$(CH_2)_g$—Y—$(CH^2)_h$—X, wherein g and h are integers between 0 and 20, wherein the sum of g and h is not greater than 20, and wherein X and Y are as defined above, —$(CH2)_i$—X—$(CH_2)_j$—Y—$(CH_2)_k$—$CH_3$, wherein i, j, and k are integers between 0 and 20, wherein the sum of i, j, and k is not greater than 20, and wherein X and Y are as defined above, and —$(CH_2)_l$—Y—$(CH_2)_m$—X—$(CH_2)_n$—$CH_3$, wherein l, m, and n are integers between 0 and 20, wherein the sum of l, m, and n is not greater than 20, and wherein X and Y are as defined above, compound and (ii) a bipyridyl compound in a first solvent to create a mixture, removing the first solvent to create a solid mass, heating the solid mass to a first temperature sufficient to provide hydrogen bonding between molecules of the 2,3 di-O-substituted tartaric acid compound and molecules of the bipyridyl compound, and cooling the solid mass, combining the solid mass with a second solvent to create a second mixture heating the second mixture to a temperature sufficient to dissolve the solid mass, cooling the second mixture to form at least one helical or tubular structure, and effecting the polymerization of the polymerizable groups.

16. The method of claim 15 wherein the bipyridyl is compound selected from the group consisting of 4,4' bipyridine and 2,2' bipyridine.

* * * * *